United States Patent [19]
Szybalski

[11] Patent Number: 5,874,259
[45] Date of Patent: Feb. 23, 1999

[54] CONDITIONALLY AMPLIFIABLE BAC VECTOR

[75] Inventor: Waclaw Szybalski, Madison, Wis.

[73] Assignee: Wisconsin Alumni Research Foundation, Madison, Wis.

[21] Appl. No.: 975,763

[22] Filed: Nov. 21, 1997

[51] Int. Cl.$^6$ ...................................................... C12P 19/34
[52] U.S. Cl. ................ 435/91.1; 435/320.1; 435/252.33
[58] Field of Search ................................ 435/320.1, 91.1, 435/252.33

[56] References Cited

PUBLICATIONS

Durland, R. et al., "Mutations in the trfA Replication Gene of the Broad–Host–Range Plasmid RK2 Result in Elevated Plasmid Copy Numbers," *Journal of Bacteriology* 172:3859–3867.

Fang, F.C. et al., "Mutations in the gene encoding the replication–initiation protein of plasmid RK2 produce elevated copy numbers of RK2 derivatives in *Escherichia coli* and distantly related bacteria," *Gene* 133:1–8 (1993).

Haugan, K. et al., The Phenotypes of Temperature–Sensitive Mini–RK2 Replicons Carrying Mutations in the Replication Control Gene trfA Are Suppressed Nonspecifically by Intragenic cop Mutations,: *Journal of Bacteriology* 174:7026–7032 (1992).

Haugan, K. et al, "The Host Range of RK2 Minimal Replicon Copy–Up Mutants is Limited by Species–Specific Differences in the Maximum Tolerable Copy Number," *Plasmid* 33:27–39 (1995).

Hamilton, Carol M., "A Binary–BAC System for Plant Transformation with High–Molecular–Weight DNA", *Gene*, 200:107–116 (1997).

Kim, et al., "Construction and Characterization of a Human Bacterial Artificial Chromosome Library", *Genomics*, 34: 213–218 (1996).

Koob, et al., "Cleaving Yeast and *Escherichia coli* Genomes at a Single Site", *Science*, 250: 271–273 (1990).

Pósfai, et al. "In vivo Excision and Amplification of Large Segments of the *Escherichia coli* Genome", *Nucleic Acids Research*, 22 (12): 2392–2398.

Shizuya, et al., "Cloning and Stable maintenance of 300–Kilobase–Pair Fragments of Human DNA in *Escherichia coli* Using an F–Factor–based Vector", *Proc. Natl. Acad. Sci.*, 89:8794–8797.

Szybalski, Waclaw, "From the Double–Helix to Novel Approaches to the Sequencing of Large Genomes", *Gene*, 135: 279–290.

Wild, et al., "A Broad–Host–Range in vivo Pop–Out and Amplification System for Generating Large Quantities of 50–to 100–kb Genomic Fragments for Direct DNA sequencing", *Gene*, 179: 181–188 (1996).

*Primary Examiner*—James Ketter
*Assistant Examiner*—Irem Yucel
*Attorney, Agent, or Firm*—Quarles & Brady LLP

[57] ABSTRACT

A system for obtaining large amounts of a genomic DNA fragment from a bacterial artificial chromosome includes a vector that has a site into which the genomic fragment can be cloned and, flanking the site are excision mediating sites. The vector also includes, between the excision mediating sites and near one of the sites, a controllable origin of replication.

9 Claims, 1 Drawing Sheet

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 7507 base pairs
    ( B ) TYPE: nucleic acid
    ( C ) STRANDEDNESS: double
    ( D ) TOPOLOGY: circular ( i i ) MOLECULE TYPE: other nucleic acid
    ( A ) DESCRIPTION: /desc = "pBeloBac11"

( x i ) SEQUENCE DESCRIPTION: SEQ ID NO:1:

| | | | | | | |
|---|---|---|---|---|---|---|
| GCGGCCGCAA | GGGGTTCGCG | TCAGCGGGTG | TTGGCGGGTG | TCGGGGCTGG | CTTAACTATG | 60 |
| CGGCATCAGA | GCAGATTGTA | CTGAGAGTGC | ACCATATGCG | GTGTGAAATA | CCGCACAGAT | 120 |
| GCGTAAGGAG | AAAATACCGC | ATCAGGCGCC | ATTCGCCATT | CAGGCTGCGC | AACTGTTGGG | 180 |
| AAGGGCGATC | GGTGCGGGCC | TCTTCGCTAT | TACGCCAGCT | GGCGAAAGGG | GGATGTGCTG | 240 |
| CAAGGCGATT | AAGTTGGGTA | ACGCCAGGGT | TTTCCCAGTC | ACGACGTTGT | AAAACGACGG | 300 |
| CCAGTGAATT | GTAATACGAC | TCACTATAGG | GCGAATTCGA | GCTCGGTACC | CGGGGATCCT | 360 |
| CTAGAGTCGA | CCTGCAGGCA | TGCAAGCTTG | AGTATTCTAT | AGTGTCACCT | AAATAGCTTG | 420 |
| GCGTAATCAT | GGTCATAGCT | GTTTCCTGTG | TGAAATTGTT | ATCCGCTCAC | AATTCCACAC | 480 |
| AACATACGAG | CCGGAAGCAT | AAAGTGTAAA | GCCTGGGGTG | CCTAATGAGT | GAGCTAACTC | 540 |
| ACATTAATTG | CGTTGCGCTC | ACTGCCCGCT | TTCCAGTCGG | GAAACCTGTC | GTGCCAGCTG | 600 |
| CATTAATGAA | TCGGCCAACG | CGAACCCCTT | GCGGCCGCCC | GGGCCGTCGA | CCAATTCTCA | 660 |
| TGTTTGACAG | CTTATCATCG | AATTTCTGCC | ATTCATCCGC | TTATTATCAC | TTATTCAGGC | 720 |
| GTAGCAACCA | GGCGTTTAAG | GGCACCAATA | ACTGCCTTAA | AAAAATTACG | CCCCGCCCTG | 780 |
| CCACTCATCG | CAGTACTGTT | GTAATTCATT | AAGCATTCTG | CCGACATGGA | AGCCATCACA | 840 |
| AACGGCATGA | TGAACCTGAA | TCGCCAGCGG | CATCAGCACC | TTGTCGCCTT | GCGTATAATA | 900 |

-continued

| | | | | | |
|---|---|---|---|---|---|
| TTTGCCCATG | GTGAAAACGG | GGGCGAAGAA | GTTGTCCATA | TTGGCCACGT | TTAAATCAAA | 960
| ACTGGTGAAA | CTCACCCAGG | GATTGGCTGA | GACGAAAAAC | ATATTCTCAA | TAAACCCTTT | 1020
| AGGGAAATAG | GCCAGGTTTT | CACCGTAACA | CGCCACATCT | TGCGAATATA | TGTGTAGAAA | 1080
| CTGCCGGAAA | TCGTCGTGGT | ATTCACTCCA | GAGCGATGAA | AACGTTTCAG | TTTGCTCATG | 1140
| GAAAACGGTG | TAACAAGGGT | GAACACTATC | CCATATCACC | AGCTCACCGT | CTTTCATTGC | 1200
| CATACGGAAT | TCCGGATGAG | CATTCATCAG | GCGGGCAAGA | ATGTGAATAA | AGGCCGGATA | 1260
| AAACTTGTGC | TTATTTTTCT | TTACGGTCTT | TAAAAAGGCC | GTAATATCCA | GCTGAACGGT | 1320
| CTGGTTATAG | GTACATTGAG | CAACTGACTG | AAATGCCTCA | AAATGTTCTT | TACGATGCCA | 1380
| TTGGGATATA | TCAACGGTGG | TATATCCAGT | GATTTTTTC | TCCATTTTAG | CTTCCTTAGC | 1440
| TCCTGAAAAT | CTCGATAACT | CAAAAAATAC | GCCCGGTAGT | GATCTTATTT | CATTATGGTG | 1500
| AAAGTTGGAA | CCTCTTACGT | GCCGATCAAC | GTCTCATTTT | CGCCAAAAGT | TGGCCCAGGG | 1560
| CTTCCCGGTA | TCAACAGGGA | CACCAGGATT | TATTTATTCT | GCGAAGTGAT | CTTCCGTCAC | 1620
| AGGTATTTAT | TCGCGATAAG | CTCATGGAGC | GGCGTAACCG | TCGCACAGGA | AGGACAGAGA | 1680
| AAGCGCGGAT | CTGGGAAGTG | ACGGACAGAA | CGGTCAGGAC | CTGGATTGGG | GAGGCGGTTG | 1740
| CCGCCGCTGC | TGCTGACGGT | GTGACGTTCT | CTGTTCCGGT | CACACCACAT | ACGTTCCGCC | 1800
| ATTCCTATGC | GATGCACATG | CTGTATGCCG | GTATACCGCT | GAAAGTTCTG | CAAAGCCTGA | 1860
| TGGACATAA | GTCCATCAGT | TCAACGGAAG | TCTACACGAA | GGTTTTGCG | CTGGATGTGG | 1920
| CTGCCCGGCA | CCGGGTGCAG | TTTGCGATGC | CGGAGTCTGA | TGCGGTTGCG | ATGCTGAAAC | 1980
| AATTATCCTG | AGAATAAATG | CCTTGGCCTT | TATATGGAAA | TGTGGAACTG | AGTGGATATG | 2040
| CTGTTTTTGT | CTGTTAAACA | GAGAAGCTGG | CTGTTATCCA | CTGAGAAGCG | AACGAAACAG | 2100
| TCGGGAAAAT | CTCCCATTAT | CGTAGAGATC | CGCATTATTA | ATCTCAGGAG | CCTGTGTAGC | 2160
| GTTTATAGGA | AGTAGTGTTC | TGTCATGATG | CCTGCAAGCG | GTAACGAAAA | CGATTTGAAT | 2220
| ATGCCTTCAG | GAACAATAGA | AATCTTCGTG | CGGTGTTACG | TTGAAGTGGA | GCGGATTATG | 2280
| TCAGCAATGG | ACAGAACAAC | CTAATGAACA | CAGAACCATG | ATGTGGTCTG | TCCTTTTACA | 2340
| GCCAGTAGTG | CTCGCCGCAG | TCGAGCGACA | GGGCGAAGCC | CTCGAGTGAG | CGAGGAAGCA | 2400
| CCAGGGAACA | GCACTTATAT | ATTCTGCTTA | CACACGATGC | CTGAAAAAAC | TTCCCTTGGG | 2460
| GTTATCCACT | TATCCACGGG | GATATTTTA | TAATTATTTT | TTTTATAGTT | TTTAGATCTT | 2520
| CTTTTTTAGA | GCGCCTTGTA | GGCCTTTATC | CATGCTGGTT | CTAGAGAAGG | TGTTGTGACA | 2580
| AATTGCCCTT | TCAGTGTGAC | AAATCACCCT | CAAATGACAG | TCCTGTCTGT | GACAAATTGC | 2640
| CCTTAACCCT | GTGACAAATT | GCCCTCAGAA | GAAGCTGTTT | TTTCACAAAG | TTATCCCTGC | 2700
| TTATTGACTC | TTTTTTATTT | AGTGTGACAA | TCTAAAAACT | TGTCACACTT | CACATGGATC | 2760
| TGTCATGGCG | GAAACAGCGG | TTATCAATCA | CAAGAAACGT | AAAAATAGCC | CGCGAATCGT | 2820
| CCAGTCAAAC | GACCTCACTG | AGGCGGCATA | TAGTCTCTCC | CGGGATCAAA | AACGTATGCT | 2880
| GTATCTGTTC | GTTGACCAGA | TCAGAAAATC | TGATGGCACC | CTACAGGAAC | ATGACGGTAT | 2940
| CTGCGAGATC | CATGTTGCTA | AATATGCTGA | AATATTCGGA | TTGACCTCTG | CGGAAGCCAG | 3000
| TAAGGATATA | CGGCAGGCAT | TGAAGAGTTT | CGCGGGGAAG | GAAGTGGTTT | TTTATCGCCC | 3060
| TGAAGAGGAT | GCCGGCGATG | AAAAAGGCTA | TGAATCTTTT | CCTTGGTTTA | TCAAACGTGC | 3120
| GCACAGTCCA | TCCAGAGGGC | TTTACAGTGT | ACATATCAAC | CCATATCTCA | TTCCCTTCTT | 3180
| TATCGGGTTA | CAGAACCGGT | TTACGCAGTT | TCGGCTTAGT | GAAACAAAAG | AAATCACCAA | 3240
| TCCGTATGCC | ATGCGTTTAT | ACGAATCCCT | GTGTCAGTAT | CGTAAGCCGG | ATGGCTCAGG | 3300

```
CATCGTCTCT CTGAAAATCG ACTGGATCAT AGAGCGTTAC CAGCTGCCTC AAAGTTACCA    3360
GCGTATGCCT GACTTCCGCC GCCGCTTCCT GCAGGTCTGT GTTAATGAGA TCAACAGCAG    3420
AACTCCAATG CGCCTCTCAT ACATTGAGAA AAAGAAAGGC CGCCAGACGA CTCATATCGT    3480
ATTTTCCTTC CGCGATATCA CTTCCATGAC GACAGGATAG TCTGAGGGTT ATCTGTCACA    3540
GATTTGAGGG TGGTTCGTCA CATTTGTTCT GACCTACTGA GGGTAATTTG TCACAGTTTT    3600
GCTGTTTCCT TCAGCCTGCA TGGATTTTCT CATACTTTTT GAACTGTAAT TTTTAAGGAA    3660
GCCAAATTTG AGGGCAGTTT GTCACAGTTG ATTTCCTTCT CTTTCCTTC GTCATGTGAC    3720
CTGATATCGG GGGTTAGTTC GTCATCATTG ATGAGGGTTG ATTATCACAG TTTATTACTC    3780
TGAATTGGCT ATCCGCGTGT GTACCTCTAC CTGGAGTTTT TCCCACGGTG GATATTTCTT    3840
CTTGCGCTGA GCGTAAGAGC TATCTGACAG AACAGTTCTT CTTTGCTTCC TCGCCAGTTC    3900
GCTCGCTATG CTCGGTTACA CGGCTGCGGC GAGCGCTAGT GATAATAAGT GACTGAGGTA    3960
TGTGCTCTTC TTATCTCCTT TTGTAGTGTT GCTCTTATTT TAAACAACTT GCGGTTTTT    4020
TGATGACTTT GCGATTTTGT TGTTGCTTTG CAGTAAATTG CAAGATTTAA TAAAAAAACG    4080
CAAAGCAATG ATTAAAGGAT GTTCAGAATG AAACTCATGG AAACACTTAA CCAGTGCATA    4140
AACGCTGGTC ATGAAATGAC GAAGGCTATC GCCATTGCAC AGTTTAATGA TGACAGCCCG    4200
GAAGCGAGGA AAATAACCCG GCGCTGGAGA ATAGGTGAAG CAGCGGATTT AGTTGGGGTT    4260
TCTTCTCAGG CTATCAGAGA TGCCGAGAAA GCAGGGCGAC TACCGCACCC GGATATGGAA    4320
ATTCGAGGAC GGGTTGAGCA ACGTGTTGGT TATACAATTG AACAAATTAA TCATATGCGT    4380
GATGTGTTTG GTACGCGATT GCGACGTGCT GAAGACGTAT TTCCACCGGT GATCGGGGTT    4440
GCTGCCCATA AAGGTGGCGT TTACAAAACC TCAGTTTCTG TTCATCTTGC TCAGGATCTG    4500
GCTCTGAAGG GGCTACGTGT TTTGCTCGTG GAAGGTAACG ACCCCCAGGG AACAGCCTCA    4560
ATGTATCACG GATGGGTACC AGATCTTCAT ATTCATGCAG AAGACACTCT CCTGCCTTTC    4620
TATCTTGGGG AAAAGGACGA TGTCACTTAT GCAATAAAGC CCACTTGCTG GCCGGGGCTT    4680
GACATTATTC CTTCCTGTCT GGCTCTGCAC CGTATTGAAA CTGAGTTAAT GGGCAAATTT    4740
GATGAAGGTA AACTGCCCAC CGATCCACAC CTGATGCTCC GACTGGCCAT TGAAACTGTT    4800
GCTCATGACT ATGATGTCAT AGTTATTGAC AGCGCGCCTA ACCTGGGTAT CGGCACGATT    4860
AATGTCGTAT GTGCTGCTGA TGTGCTGATT GTTCCCACGC CTGCTGAGTT GTTTGACTAC    4920
ACCTCCGCAC TGCAGTTTTT CGATATGCTT CGTGATCTGC TCAAGAACGT TGATCTTAAA    4980
GGGTTCGAGC CTGATGTACG TATTTTGCTT ACCAAATACA GCAATAGTAA TGGCTCTCAG    5040
TCCCCGTGGA TGGAGGAGCA AATTCGGGAT GCCTGGGGAA GCATGGTTCT AAAAAATGTT    5100
GTACGTGAAA CGGATGAAGT TGGTAAAGGT CAGATCCGGA TGAGAACTGT TTTTGAACAG    5160
GCCATTGATC AACGCTCTTC AACTGGTGCC TGGAGAAATG CTCTTTCTAT TTGGGAACCT    5220
GTCTGCAATG AAATTTTCGA TCGTCTGATT AAACCACGCT GGGAGATTAG ATAATGAAGC    5280
GTGCGCCTGT TATTCCAAAA CATACGCTCA ATACTCAACC GGTTGAAGAT ACTTCGTTAT    5340
CGACACCAGC TGCCCCGATG GTGGATTCGT TAATTGCGCG CGTAGGAGTA ATGGCTCGCG    5400
GTAATGCCAT TACTTTGCCT GTATGTGGTC GGGATGTGAA GTTACTCTT GAAGTGCTCC    5460
GGGGTGATAG TGTTGAGAAG ACCTCTCGGG TATGGTCAGG TAATGAACGT GACCAGGAGC    5520
TGCTTACTGA GGACGCACTG GATGATCTCA TCCCTTCTTT TCTACTGACT GGTCAACAGA    5580
CACCGGCGTT CGGTCGAAGA GTATCTGGTG TCATAGAAAT TGCCGATGGG AGTCGCCGTC    5640
GTAAAGCTGC TGCACTTACC GAAAGTGATT ATCGTGTTCT GGTTGGCGAG CTGGATGATG    5700
```

-continued

| | | | | | |
|---|---|---|---|---|---|
| AGCAGATGGC | TGCATTATCC | AGATTGGGTA | ACGATTATCG | CCCAACAAGT | GCTTATGAAC | 5760
| GTGGTCAGCG | TTATGCAAGC | CGATTGCAGA | ATGAATTTGC | TGGAAATATT | TCTGCGCTGG | 5820
| CTGATGCGGA | AAATATTTCA | CGTAAGATTA | TTACCGCTG | TATCAACACC | GCCAAATTGC | 5880
| CTAAATCAGT | TGTTGCTCTT | TTTTCTCACC | CCGGTGAACT | ATCTGCCCGG | TCAGGTGATG | 5940
| CACTTCAAAA | AGCCTTTACA | GATAAAGAGG | AATTACTTAA | GCAGCAGGCA | TCTAACCTTC | 6000
| ATGAGCAGAA | AAAGCTGGG | GTGATATTTG | AAGCTGAAGA | AGTTATCACT | CTTTTAACTT | 6060
| CTGTGCTTAA | AACGTCATCT | GCATCAAGAA | CTAGTTTAAG | CTCACGACAT | CAGTTTGCTC | 6120
| CTGGAGCGAC | AGTATTGTAT | AAGGGCGATA | AAATGGTGCT | TAACCTGGAC | AGGTCTCGTG | 6180
| TTCCAACTGA | GTGTATAGAG | AAAATTGAGG | CCATTCTTAA | GGAACTTGAA | AAGCCAGCAC | 6240
| CCTGATGCGA | CCACGTTTTA | GTCTACGTTT | ATCTGTCTTT | ACTTAATGTC | CTTTGTTACA | 6300
| GGCCAGAAAG | CATAACTGGC | CTGAATATTC | TCTCTGGGCC | CACTGTTCCA | CTTGTATCGT | 6360
| CGGTCTGATA | ATCAGACTGG | GACCACGGTC | CCACTCGTAT | CGTCGGTCTG | ATTATTAGTC | 6420
| TGGGACCACG | GTCCCACTCG | TATCGTCGGT | CTGATTATTA | GTCTGGGACC | ACGGTCCAC | 6480
| TCGTATCGTC | GGTCTGATAA | TCAGACTGGG | ACCACGGTCC | CACTCGTATC | GTCGGTCTGA | 6540
| TTATTAGTCT | GGGACCATGG | TCCCACTCGT | ATCGTCGGTC | TGATTATTAG | TCTGGGACCA | 6600
| CGGTCCCACT | CGTATCGTCG | GTCTGATTAT | TAGTCTGGAA | CCACGGTCCC | ACTCGTATCG | 6660
| TCGGTCTGAT | TATTAGTCTG | GGACCACGGT | CCCACTCGTA | TCGTCGGTCT | GATTATTAGT | 6720
| CTGGGACCAC | GATCCCACTC | GTGTTGTCGG | TCTGATTATC | GGTCTGGGAC | CACGGTCCCA | 6780
| CTTGTATTGT | CGATCAGACT | ATCAGCGTGA | GACTACGATT | CCATCAATGC | CTGTCAAGGG | 6840
| CAAGTATTGA | CATGTCGTCG | TAACCTGTAG | AACGGAGTAA | CCTCGGTGTG | CGGTTGTATG | 6900
| CCTGCTGTGG | ATTGCTGCTG | TGTCCTGCTT | ATCCACAACA | TTTTGCGCAC | GGTTATGTGG | 6960
| ACAAAATACC | TGGTTACCCA | GGCCGTGCCG | GCACGTTAAC | CGGGCTGCAT | CCGATGCAAG | 7020
| TGTGTCGCTG | TCGACGAGCT | CGCGAGCTCG | GACATGAGGT | TGCCCCGTAT | TCAGTGTCGC | 7080
| TGATTTGTAT | TGTCTGAAGT | TGTTTTACG | TTAAGTTGAT | GCAGATCAAT | TAATACGATA | 7140
| CCTGCGTCAT | AATTGATTAT | TTGACGTGGT | TTGATGGCCT | CCACGCACGT | TGTGATATGT | 7200
| AGATGATAAT | CATTATCACT | TTACGGGTCC | TTTCCGGTGA | TCCGACAGGT | TACGGGGCGG | 7260
| CGACCTCGCG | GGTTTTCGCT | ATTTATGAAA | ATTTTCCGGT | TTAAGGCGTT | TCCGTTCTTC | 7320
| TTCGTCATAA | CTTAATGTTT | TTATTTAAAA | TACCCTCTGA | AAAGAAAGGA | AACGACAGGT | 7380
| GCTGAAAGCG | AGCTTTTTGG | CCTCTGTCGT | TTCCTTTCTC | TGTTTTTGTC | CGTGGAATGA | 7440
| ACAATGGAAG | TCCGAGCTCA | TCGCTAATAA | CTTCGTATAG | CATACATTAT | ACGAAGTTAT | 7500
| ATTCGAT | | | | | | 7507

(2) INFORMATION FOR SEQ ID NO:2:

(i) SEQUENCE CHARACTERISTICS:
        (A) LENGTH: 520 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

| | | | | | |
|---|---|---|---|---|---|
| CCGGCGTTGT | GGATACCACG | CGGAAAACTT | GGCCCTCACT | GACAGATGAG | GGGCGGACGT | 60
| TGACACTTGA | GGGGCCGACT | CACCCGGCGC | GGCGTTGACA | GATGAGGGGC | AGGCTCGATT | 120

-continued

| | | | | | | |
|---|---|---|---|---|---|---|
| TCGGCCGGCG | ACGTGGAGCT | GGCCAGCCTC | GCAAATCGGC | GAAAACGCCT | GATTTTACGC | 180 |
| GAGTTTCCCA | CAGATGATGT | GGACAAGCCT | GGGGATAAGT | GCCCTGCGGT | ATTGACACTT | 240 |
| GAGGGGCGCG | ACTACTGACA | GATGAGGGGC | GCGATCCTTG | ACACTTGAGG | GGCAGAGTGA | 300 |
| TGACAGATGA | GGGGCGCACC | TATTGACATT | TGAGGGGCTG | TCCACAGGCA | GAAAATCCAG | 360 |
| CATTTGCAAG | GGTTTCCGCC | CGTTTTTCGG | CCACCGCTAA | CCTGTCTTTT | AACCTGCTTT | 420 |
| TAAACCAATA | TTTATAAACC | TTGTTTTTAA | CCAGGGCTGC | GCCCTGGCGC | GTGACCGCGC | 480 |
| ACGCCGAAGG | GGGGTGCCCC | CCCTTCTCGA | ACCCTCCCGG | | | 520 |

(2) INFORMATION FOR SEQ ID NO:3:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

| | | | |
|---|---|---|---|
| GAAGTTCCTA | TTCTCTAGAA | AGTATAGGAA | CTTC | 34 |

CONDITIONALLY AMPLIFIABLE BAC VECTOR

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Efforts to determine the nucleotide sequence of complete genomes, or a large portion thereof, have traditionally taken a so-called bottom-up approach, including the steps of mapping the genome, preparing a library of random large clones in yeast artificial chromosomes (YACs), bacterial artificial chromosomes (BACs), P1 or cosmids, followed by random subcloning in M13-like vectors. Among such systems, BACs are at present the preferred vector for maintaining large genomic DNA fragments. BACs are preferred because individual DNA fragments are maintained stably in a single copy vector in the host cells, even after 100 or more generations of serial growth. In contrast, the DNA fragments cloned into YACs tend to be unstable and can yield chimeric clones. It is difficult to recover DNA clones from YACs in a pure form.

BAC (or pBAC) vectors typically accommodate inserts in the range of approximately 30 to 300 kilobase pairs. A widely used BAC vector, pBeloBac11, uses a complementation of the lacZ gene to distinguish insert-containing recombinant molecules from colonies carrying the BAC vector, by color. When a DNA fragment is cloned into the lacZ gene of pBeloBac11, insertional activation results in a white colony on X-Gal/IPTG plates after transformation. Kim, U-J et al., "Construction and Characterization of a Human Bacterial Artificial Chromosome Library," *Genomics* 34:213–218 (1996). Thus, it is now possible to distinguish those colonies that contain BACs with inserts from those that lack inserts. A similar prior vector, pBAC108L, lacked the ability to distinguish insert-containing BACs. Shizuya, H., "Cloning and stable maintenance of 300-kilobase-pair fragments of human DNA in *Escherichia coli* using an F-factor-based vector," P.N.A.S. U.S.A. 89:8794–8797 (1992).

Although these single-copy vectors are advantageously used to clone large genomic DNA fragments for subsequent analysis, especially sequence analysis, the single-copy nature of these vectors is also a limitation in that large numbers of cells containing a BAC clone of interest must be grown to produce a sufficient quantity for subsequent analysis. It is, of course, possible to amplify portions of a BAC clone of interest using, a for example, PCR, but simple amplification of the entire insert from a BAC vector has not previously been possible.

In 1993, Szybalski proposed a system for fragment-by-fragment sequencing of entire bacterial genomes by in vivo excision and subsequent amplification of the excised genomic fragments. Szybalski, W., "From the Double-Helix to Novel Approaches to the Sequencing of Large Genomes," Gene 135:279–290 (1993). One aspect of the Szybalski (1993) system is that the excision from the bacterial chromosome and the amplification of the excised genomic fragment be controlled very stringently so that excision is induced only on command and amplification is initiated only upon induction.

According to the proposed system, excision-mediating sites (EMS) are placed at 500–100 kb intervals throughout a well mapped genome in places where the EMS do not interfere with viability or genomic stability. The EMS are placed throughout the system either by (1) randomly inserting plasmids carrying transposons, EMS, and selective markers, or (2) by targeting insertions that inactivate specific, non-essential genes. EMS identified by Szybalski include $\lambda$ att, $2\mu$ FRT, and P1 lox.

The net result of adding EMS to a genome in the Szybalski (1993) system is a library of strains, each of which carries one EMS at a physically mapped site. Using genetic crosses between strains having neighboring EMS at a suitable distance from one another, a set of strains are produced where each strain possesses exactly two neighboring EMS. From such strains, the intervening segment (e.g., 50–100 kb), can be excised. Accordingly to the Szybalski 1993 system, if a cis-acting ori element is positioned together with and next to the excision elements, the ori element will be present on the excised DNA circle and can promote the amplification of the DNA circle.

Szybalski (1993) does not contemplate employing an amplification and excision system in conjunction with a bacterial artificial chromosome. Such a system would provide additional benefit in that it would not require the steps of interspersing EMS throughout the genome and crossing EMS-containing strains, but could instead rely upon the use of rare-cutting restriction enzymes to generate genomic fragments of suitable size for cloning into a BAC vector.

BRIEF SUMMARY OF THE INVENTION

In a first aspect, the present invention is an improved bacterial artificial chromosome (BAC) cloning vector (pBAC) that comprises a pair of excision-mediating sites (EMS) provided in parallel orientation to one another and flanking a site into which a genomic fragment insert can be cloned (which can be a multiple cloning site) one EMS being 5' and a second EMS being downstream of the cloning site. In the presence of a suitable signal in a suitable host cell, the EMS of an insert-containing BAC clone are conditionally activated to recombine with one another and thereby excise the nucleic acid therebetween to produce a circular plasmid that comprises the genomic fragment insert. Both the EMS and origin of replication (ori) are responsive to trans-acting signals that direct the fragment to be excised from the vector and to be amplified by replication.

Also provided on the same fragment of the BAC vector between the EMS, and close to one of the EMS, is an ori that can be conditionally activated in the host cell in which the BAC vector is maintained. The conditional ori is positioned such that it resides on the plasmid excised from the BAC clone in the excision step. In response to a suitable signal in the host cell, replication is initiated at the ori and the excised plasmid is amplified and accumulates in the cell at high-copy number.

Any BAC vector can be improved in accordance with the present invention. Before being improved, the BAC vector must be capable of independent replication in the host cells. The vector should therefore include an ori that functions in the host cells, as well as any other genes that encode proteins required for plasmid replication, maintenance, and partitioning. The vector can contain a selectable marker such as a chloramphenicol-resistance gene, and at least one cloning site into which the genomic fragments can be cloned. The vector also preferably contains a gene that can be disrupted by inserting a genomic fragment into the cloning site, thereby imparting an ability to distinguish clones that contain a genomic insert from those that lack a genomic insert, preferably on the basis of color.

A preferred starting vector that can be modified in accordance with the invention is either pBAC108L (Shizuya, H., et al., supra) or pBeloBAC11 (Kim, U-J, et al., supra), both publications being incorporated herein by reference. Modifications in accordance with the present invention are described relative to pBeloBac11, although one skilled in the art can readily make the same changes to other plasmids including, but not limited to, pBac108L.

In a second aspect, the invention is a host cell comprising in its interior the improved BAC vector of the present invention, where the host cell can conditionally provide the signals required to excise and amplify the insert from the BAC vector. The host cell is preferably bacterial, such as $E.$ $coli$, but can be a plant, yeast, or animal cell, including a mammalian cell, as long as the EMS and the ori in the BAC vector, and the activating functions in the host cell are selected so as to function in the selected host. Hamilton, C. M., "A Binary-BAC system for plant transformation with high-molecular weight DNA," $Gene$ 200:107–116 (1997) describes a BAC vector for use in plant cells.

In a third aspect, the invention is a method for amplifying in a host cell a genomic DNA insert in a BAC vector modified in accordance with the invention. The method includes the steps of (1) providing in the host cell a first signal that directs excision of the genomic DNA insert at the EMSs to form an first plasmid that comprises the excised insert and an ori competent in the host cell, and a second plasmid that comprises the BAC vector backbone, and (2) providing in the host cell a second signal that directs amplification of the excised plasmid to replicate, thereby producing multiple copies of itself.

Existing pBAC vectors could alternatively also be improved simply by providing a conditional ori on the vector. Such a modified vector (with insert) would be maintained at a single copy, but could be amplified in its entirety upon command. Such a vector could be prepared as described herein, except there would be no need to provide the EMS or the excision-mediating protein. A conditional activator of the ori would still be required, and could be provided as described herein.

It is an object of the present invention to retain the advantageous properties of existing BAC vectors.

It is another object of the present invention to provide a bacterial artificial chromosome that can, in the presence of an appropriate first signal, excise a sequence of interest from the BAC which can, in the presence of a second signal, amplify the insert to a copy number of between 10 and 500 copies or higher.

It is yet another object of the present invention to provide a vector that can be conditionally amplified in the presence of an appropriate signal.

It is a feature of the present invention that the BAC vector includes a pair of excision mediating sites (EMS) flanking a site into which genomic DNA fragments can be cloned and furthermore contain a conditional ori near one EMS and in any event between the pair of EMS that flank the cloned gene.

It is an advantage of the present invention that an abundance of a target insert in a BAC can be selectively replicated by providing appropriate signals to the host cell.

Other objects, advantages, and features of the present invention will become apparent upon consideration of the following detailed description taken in conjunction with the accompanying drawings.

DETAILED DESCRIPTION OF THE INVENTION

Figure 1:
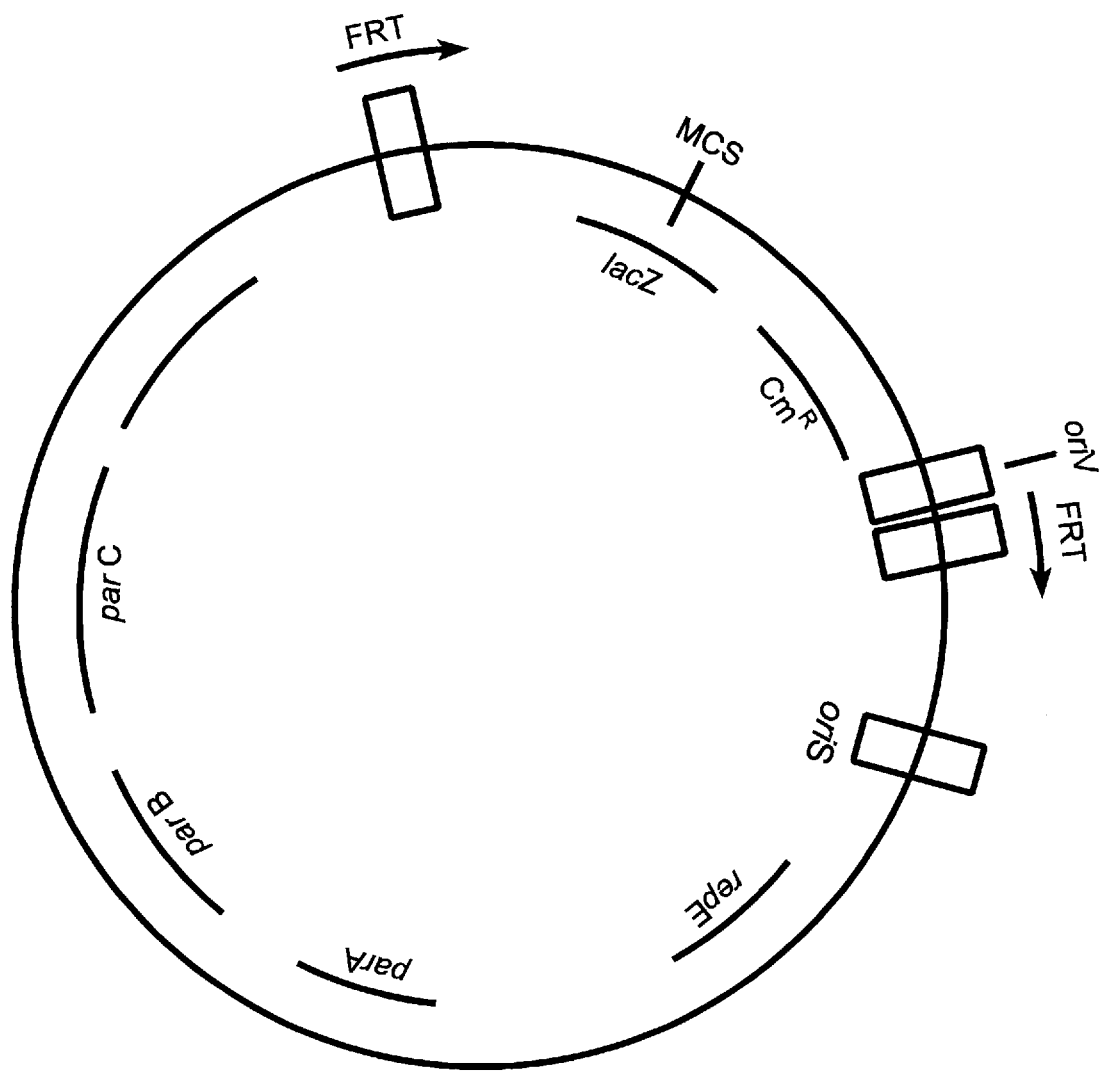
FIG. 1 schematically depicts a vector prepared in accordance with the present invention.

Shown in SEQ ID NO:1 is the sequence of starting vector pBeloBAC11 as reported at GenBank Accession Number U51113, the record of which is incorporated herein by reference. SEQ ID NO:1 is a circular plasmid sequence that includes oriS, the repE gene that produces a protein that initiates replication at oriS, and partition genes parA, B, and C. For selection, pBeloBAC11 includes a chloramphenicol-resistance-encoding gene ($Cm^R$). The vector also includes a lacZ gene that can be disrupted or eliminated from the vector when an insert is cloned.

In accordance with the improvement, a first insertion, a combined EMS/ori element, can be made at the unique XhoI site of pBeloBAC11 at nucleotide 2381. It is not essential that the EMS and the ori be immediately adjacent to one another, although this can be convenient in the laboratory. It is essential, however, that the ori element is more proximal than the FRT element to the MCS so that the conditional ori element is provided on the same segment of the BAC vector as the cloning site. In the preferred embodiment, the selected EMS was an FRT sequence element derived from the 2, yeast plasmid. A yeast 2 $\mu$ FRT element (SEQ ID NO:3) includes a pair of specific 13-base pair nearly-perfect inverted repeats with an 8-base pair spacer between the inverted repeats. This short sequence is the target for the yeast Flp protein. Other EMS are also equally well suited to be used to modify the BAC vector in accordance with the invention. Among others, the $\lambda$ att and P1 lox sequences are also suitable.

The preferred conditional ori is oriV, although the conditional ori could be any ori that functions in the host cell and is responsive to the amplification-mediating protein(s). It is preferable, for the sake of simplicity that the ori respond to a single protein, although this is not essential, and multi-protein replication systems are known. It is preferable that the ori amplify the plasmid to high copy number where the goal is to produce large quantities of DNA. The oriV is preferred because of its broad host range, its known capacity to replicate DNA fragments of 100-kb or larger, its high copy number and its requirement for only one inducing protein.

To make this insertion in the preferred embodiment, the oriV element of SEQ ID NO:2 and the FRT element of SEQ ID NO:3 were ligated together and the resulting fragment was made blunt ended and then ligated into the XhoI site which had been made blunt ended. The orientation of the two joined fragments is such that when the fragment is cloned into the XhoI site, the ori is physically located between the nearby FRT site and the insert cloning site.

A second EMS can be inserted by blunt end ligation into HpaI-cleaved pBeloBAC11 that had previously been blunted using Klenow fragment. In the preferred embodiment, the EMS was provided on a HpaI-SalI fragment where the SalI end was blunted. It is important that the EMS be inserted in parallel orientation to the EMS inserted to the opposite side of the cloning site. Since excision will occur only if the two EMS are in parallel orientation, one can readily determine whether the proper insertion has been made by performing the excision assay noted below. If excision is not noted, then the second EMS is not in parallel with the first and is not appropriate for further use according to the invention.

The resulting improved vector, depicted schematically in FIG. 1, can receive genomic DNA fragments to produce libraries in exactly the same manner as for pBeloBac11. Insert-containing clones of interest can be obtained for further analysis from the resulting libraries using the same techniques as are described in Kim, U-J., et al. supra, incorporated herein by reference.

An advantage of the present invention is that in addition to its capacity to maintaining (and yielding) only a single copy of the cloned fragment, multiple copies can be easily produced without requiring additional cloning steps. Once an insert-containing clone of interest is identified, the conditional excision and amplification of the present invention can be induced, but only on command. To excise the fragment of interest, the cells containing the BAC vector are induced to produce the excision-mediating protein. If the FRT sequence is the EMS, the yeast Flp protein is provided. In the presence of Flp, which interacts with the pair of parallel FRT sites, the fragment of interest is excised and circularized. Since the excised insert-containing plasmid contains the conditional ori, in the presence of the amplification-mediating replication protein(s) the plasmid is induced to replicate from the conditional ori until it reaches its maximal copy number, which can typically range between 10 and 500. In the preferred embodiment, employing the oriV, the plasmid is induced to replicate to high copy number in the presence of TrfA protein. The sequence of TrfA is known as is the sequence of the gene that encodes TrfA. In the preferred embodiment, copy-up mutant trfA278D was employed, although others could be used.

Several suitable means exist for providing the excision-mediating and amplification-mediating functions in the host cell that contains the modified BAC with insert. Since the excision and amplification are only desired at a certain circumstance or stage in the process, the genes that encode the required proteins are under tight regulatory control, without regard to the means by which the functions are provided. In the exemplified embodiment, the FLP and trfA genes were provided adjacent to one another in a cassette under the transcriptional control of the $P_{tet}$ promoter which can itself be repressed by the TetR protein. The tetr gene was provided, to ensure the presence of TetR. When the TetR repressor activity is eliminated, in the presence of autoclaved chlortetracycline, the genes that encode the excision- and amplification-mediating proteins are transcribed and translated, whereupon excision and amplification of the cloned fragment can proceed.

A first means for providing the controlled activation requires the host cell chromosome to include the genes that encode both functions, and this method is considered preferred by the inventor, since it does not require the maintenance of a delivery plasmid. To insert the above-noted cassette into the host genome, the cassette can simply be provided on a plasmid that also includes an attP integration site, a temperature-sensitive ori, and an antibiotic-resistance-encoding gene such as a gene encoding kanamycin resistance. The plasmid can be transformed into a host cell such as E. coli DH5α. The cells are grown at a permissive temperature and then are shifted to a replication-limiting temperature such as 42° C. In the presence of λ Int integration protein (encoded by the same or a second plasmid), recombination can proceed between the attP site of the plasmid and the attB site of the bacterial chromosome of the host cell. Colonies that contain a chromosome with the integrated cassette can be obtained by selecting antibiotic-resistant colonies that can grow at 42° C. The unintegrated plasmid will not persist at the elevated temperature, since it can only replicate at the permissive temperature, and thus it will become diluted.

If the genes that activate the excision and amplification functions are not provided in the host cell chromosome, a comparable regulated cassette can be provided on a low-, medium-, or high-copy number plasmid that resides within the host cell. The cassette can readily be ligated into a backbone of, for example, low-copy-number plasmid RSF1010, medium-copy-number plasmid pBR322, or high-copy-number plasmid pBBR1 in a manner known to one skilled in the art, where the backbone provides the plasmid replication functions. The plasmids can be introduced into a host cell, typically an E. coli cell, and preferably E. coli DH5α by a standard transformation procedure. In addition to varying copy numbers, the delivery plasmid that supplies the trans-activating functions can be chosen on the basis of host range. Procedures for preparing such plasmids and for delivering the plasmids into host cells are described in Wild, J. et al., Gene 179:181–188 (1997), and particularly the references cited in the legend accompanying FIG. 4 thereof, all of which are incorporated herein by reference.

In the method of the present invention, BAC libraries are prepared using the vector of the present invention using the same techniques as are now presently employed using e.g., pBeloBac11 or other pBAC vectors. See, Shizuya, H. et al., supra and Kim, U-J., et al., supra, both incorporated herein by reference. Briefly, size selected high-molecular-weight DNA is partially or completely digested with a rare-cutting restriction endonuclease such as NotI, and the size-selected DNA is ligated into the vector of the present invention at an approximately 10:1 molar ratio of insert DNA:vector in the presence of a DNA ligase such as T4 DNA ligase. After overnight incubation at 16° C., the ligations are dialyzed for two hours at room temperature against 0.5×TE buffer and are transferred into host cells (capable of providing the transacting functions upon suitable induction), preferably by electroporation. The mixture of transformed cells is allowed to recover and is then plated, preferably in the presence of a color indicator system such as X-Gal/IPTG.

Library screening is accomplished as previously described in the above-incorporated papers. When a clone of interest is identified for further analysis, the cells of the clone are grown overnight in LB medium supplemented with appropriate antibiotics to ensure that the cell maintains both the BAC clone as well as the delivery plasmid (if required).

The overnight cultures are used to inoculate fresh M9 minimal medium [Sambrook, J., et al., "Molecular Cloning: A Laboratory Manual," Second Edition CSHL Press, Cold Spring Harbor, N.Y. (1989)] supplemented with 2% glycerol (as a carbon source)/0.1% casamino acids, and antibiotics (ampicillin, chloramphenicol, and kanamycin). Cultures are grown at 30° C. in a water bath shaker until the $A_{590}$ reached 0.4– 0.5. To induce synthesis of the trans-activating genes, 10 μg of chlortetracycline, which is autoclaved for thirty minutes prior to use, is added (per ml), and the incubation is continued overnight. During this incubation, the fragment between the FRT sites that contains the cloning site and the conditional ori is excised from the BAC clone and amplified to the levels described.

DNA is extracted from the overnight cultures by alkaline lysis. Samples are purified by extraction with phenol/ chloroform/isoamyl alcohol, and are precipitated with ethanol. DNA from a 3 ml culture was resuspended in 30 μl of TE buffer. Although it is preferred that the resulting DNA be somewhat purified before further analysis, especially if the DNA will be fragmented for use in shotgun cloning, purification is not considered an essential step of the process. Purification may not be required for subsequent use of the DNA for sequence analysis by primer walking.

The present invention will be better understood upon consideration of the following non-limiting example.

EXAMPLE

In a test of the method and improved vector of the present invention, the modified BAC vector was introduced into DH5 host cells that comprised in their genome the FLP and trfa genes under control of the repressed ptet promoter. The cells were either not induced (control) or induced with autoclaved chlortetracycline (cTc). DNA was obtained from the control and induced host cells as described herein, and was cleaved with NcoI.

NcoI-digested uninduced vector produced only two fragments, long and short, which can be resolved visually from one another after electrophoresis. As a result of the location of the two NcoI sites and the two FRT sites in the test vector, the resulting excised plasmid and the BAC backbone plasmid each contain a single NcoI site. After induction, both of the newly created plasmids were clearly visible after electrophoresis as new bands in addition to the residual long and short bands noted above (see control) which are maintained because the excision reaction is not 100% efficient. Notably, the band that corresponds to the fragment that contains the oriV and the cloning site is wider and brighter than any other band, even despite its smaller size. This is indicative of targeted amplification of that one oriV-containing and excised plasmid, as would be expected.

Thus it is shown that a system for excising and amplifying an insert from a BAC clone in a tightly controlled manner is an advantageous improvement over existing pBAC systems and a vector that includes excision mediating sites flanking both a site into which a genomic clone can be inserted and a tightly controlled ori, is also an improvement over existing pBAC vectors.

I claim:

1. A bacterial artificial chromosome comprising
a site into which an DNA fragment can be cloned;
a pair of inducible excision-mediating sites flanking the site into which the DNA fragment can be cloned, the excision-mediating sites being provided in parallel orientation relative to one another and defining an excisable fragment that comprises the site into which the DNA fragment can be cloned; and
an inducible origin of replication on the excisable fragment.

2. A bacterial artificial chromosome as claimed in claim 1 wherein the pair of excision-mediating sites are FRT sites.

3. A bacterial artificial chromosome as claimed in claim 1 wherein the pair of excision-mediating sites comprise a sequence as shown in SEQ ID NO:3.

4. A bacterial artificial chromosome as claimed in claim 1 wherein the inducible origin of replication is oriV.

5. A cell comprising in its interior a bacterial artificial chromosome that comprises a site into which an DNA fragment can be cloned, a pair of inducible excision-mediating sites flanking the site into which the DNA fragment can be cloned, the excision-mediating sites being provided in parallel orientation relative to one another and defining an excisable fragment that comprises the site into which the DNA fragment can be cloned, and an inducible origin of replication on the excisable fragment;
a gene encoding an excision-mediating protein that induces the excisable fragment to excise from the bacterial artificial chromosome and circularize to form an excised plasmid; and
a gene encoding an amplification-mediating protein that induces the excised plasmid to replicate.

6. A cell as claimed in claim 5 wherein the gene encoding the excision-mediating protein is a FLP gene.

7. A cell as claimed in claim 5 wherein the gene encoding the amplification-mediating protein is selected from a group consisting of a trfA gene and a mutant thereof that encodes an amplication-mediating protein.

8. A method for amplifying in a cell an insert in a bacterial artificial chromosome, the insert being provided on an excisable fragment between a pair of inducible excision-mediating sites, the excisable fragment further comprising an inducible origin of replication, the method comprising the steps of:

providing in the host cell an excision-mediating protein that induces the excisable fragment to excise from the bacterial artificial chromosome and to circularize to form an excised plasmid; and providing in the host cell an amplification-mediating protein that induces the excised plasmid that comprises the insert to replicate.

9. A bacterial artificial chromosome comprising an inducible origin of replication.

* * * * *